(12) United States Patent
Li

(10) Patent No.: US 10,172,367 B2
(45) Date of Patent: Jan. 8, 2019

(54) LACTOBACILLUS PLANTARUM AND USE THEREOF

(71) Applicant: BEIJING KEHUITONGZHIHUI TECHNOLOGY CO., LTD., Beijing (CN)

(72) Inventor: Zheng Li, Tianjin (CN)

(73) Assignee: NINGXIA RISINGMARK INTELLECTUAL PROPERTY CONSULTING CO., LTD., Ningxia (CN)

( * ) Notice: Subject to any disclaimer, the term of this patent is extended or adjusted under 35 U.S.C. 154(b) by 622 days.

(21) Appl. No.: 14/844,528

(22) Filed: Sep. 3, 2015

(65) Prior Publication Data
US 2016/0029653 A1 Feb. 4, 2016
US 2017/0006888 A9 Jan. 12, 2017

(30) Foreign Application Priority Data

Sep. 18, 2014 (CN) .......................... 2014 1 0478590

(51) Int. Cl.
| | | |
|---|---|---|
| A23B 7/155 | (2006.01) | |
| A23B 7/10 | (2006.01) | |
| C12R 1/25 | (2006.01) | |
| C12N 1/20 | (2006.01) | |

(52) U.S. Cl.
CPC ................ A23B 7/155 (2013.01); A23B 7/10 (2013.01); C12N 1/20 (2013.01); C12R 1/25 (2013.01); *A23V 2002/00* (2013.01); *A23Y 2220/67* (2013.01)

(58) Field of Classification Search
None
See application file for complete search history.

(56) References Cited

U.S. PATENT DOCUMENTS 9,833,485 B2 * 12/2017 Shao .................... A61K 36/062

FOREIGN PATENT DOCUMENTS

| CN | 101720901 A | 6/2010 |
| CN | 102899262 A | 1/2013 |
| CN | 104312941 * | 1/2015 |

OTHER PUBLICATIONS

Hyun-Dong Paik et al. Meat Science, Aug. 2014, vol. 97, pp. 609-614.*

* cited by examiner

*Primary Examiner* — Vera Afremova

(57) ABSTRACT

A novel *Lactobacillus plantarum* and use thereof are disclosed, which fall within the technical field of microorganisms. The *Lactobacillus plantarum* tlj-2014 is deposited in China General Microbiological Culture Collection Center (CGMCC) under CGMCC Accession No. 9405. With the strain, the lactic acid production rate can be up to 35 g/L/d, and the concentration of lactic acid after 71 hrs of fermentation is up to 95 g/L. The *Lactobacillus plantarum* is acid tolerant, survives well at pH 1.80, can degrade the nitrite quickly with a decomposition capability of up to 9.8 mg/h/kg, and is tolerant to 1% bile salt. When the strain is used in production of pickles, the nitrite concentration is less than 5 mg/kg throughout the entire fermentation process, which is far below the content specified in the national standard GB2714-2003.

3 Claims, No Drawings

LACTOBACILLUS PLANTARUM AND USE THEREOF

CROSS-REFERENCE TO RELATED APPLICATION

This application claims the priority of Chinese Patent No. 201410478590.9 filed on Sep. 18, 2014 and entitled "Novel *Lactobacillus plantarum* and Use Thereof".

TECHNICAL FIELD

The present invention falls within the technical field of microorganisms, and more specifically relates to a novel *Lactobacillus plantarum* and use thereof.

BACKGROUND

Lactic acid bacteria (LAB) are a generic term of a class of bacteria with which large quantities of lactic acid can be produced from fermentable carbohydrates. This class of bacteria is widely distributed in nature, is abundant in species diversity, and has great application value in many important areas intimately related to human life including industry, agriculture and animal husbandry, food, medicines, and others. The use of lactic acid bacteria in food can increase the nutritive value, improve the flavor, and enhance the preservation and added value of the food. Also numerous studies suggest that the lactic acid bacteria may regulate the normal bacteria flora and maintain the micro-ecological balance in the gastrointestinal tract of an organism, enhance the digestion rate and biological value of the food, reduce the serum cholesterol, manage the endotoxins, inhibit the growth and reproduction of spoilage organisms and the production of spoilages in the intestine, produce nutritive substances, and promote tissue development, thus exerting an effect on the nutritional status, physiological functions, cell infection, drug effect, toxic reaction, immune response, tumor formation, aging process and sudden emergency response of an organism. As such, the physiological functions of the lactic acid bacteria are closely linked with the vital activities of the organism. It is believed that once cessation of growth of the lactic acid bacteria occurs, human beings and animals are hard to survive healthily. Accordingly, the lactic acid bacteria are widely used in a variety of light industries, food, medicine, and feed industry etc.

Pickles are typical traditional special fermented food in China, which are long in history, and deeply rooted in culture. Pickles have the effects of invigorating the spleen and increasing the appetite because they are tender, crisp, and refreshing, and have sour and sweet delicious tastes, thus being popular and favored by most of the consumers. Sichuan pickles are made mainly through fermentation with lactic acid bacteria, during which alcoholic fermentation, acetic fermentation, and other actions of organisms exist. The pickles are produced by cold processing, which is highly beneficial to the preservation of the nutritional ingredients, the color, and the flavor of the vegetables.

At present, the pickles are produced through conventional spontaneously inoculated fermentation or through pure culture fermentation by artificially inoculating *Lactobacillus*. The pickles produced through artificially inoculated fermentation are superior to those produced by spontaneously inoculated fermentation in terms of the improvement of the stability of the product quality, the shortening of the fermentation and production cycle, and the maintenance of the stability of the fermentation environment. However, if the tolerance of the start culture for artificial inoculation to the environment is insufficient, the color and flavor of the pickles and especially the number of the viable bacteria are affected. In Chinese Patent Publication No. CN 101720901S, pickles produced through fermentation with a starter culture and production method thereof, and more particularly pickles produced through fermentation with several pure lactic acid bacteria as starter cultures and production method thereof are disclosed. In the patent, the strains used for fermentation are *Lactobacillus plantarum* LP-115, *Leuconostoc mesenteroides* LM-57, and *Pediococcus acidilactici* P-751, which have a low tolerance to the environment, and tend to suffer from decreased number of viable bacteria during the storage and selling of the pickles, so that the healthcare functions of the viable bacteria cannot be highly exerted.

During the fermentation of the pickles, a safety problem that is difficult to overcome exists, that is, the production of the nitrite. Because the vegetables can easily accumulate nitrogen from the soil during growth, from which the nitrate is formed. The nitrate in the vegetables is reduced to form a nitrite during the process of anaerobic fermentation. The nitrite is very harmful to human body, poisoning may occur upon uptake in an amount of 0.2-0.5 g, and the nitrite is also a precursor of the highly carcinogenic substance nitrosamine. Therefore, there is a need for seeking a method for reducing the nitrite content in the pickles. In Chinese Patent Publication No. CN 102899262A, a *Lactobacillus plantarum* and a method for rapidly degrading the nitrite during fermentation by using the same are disclosed. In the method, the seed liquid of expanded *Lactobacillus plantarum* is inoculated in fermentation of *Capsicum chinense*, and 12% of high salt is added for flavoring after fermentation. The nitrite content in the *Capsicum chinense* fermented by using the method is significantly lowered, and the original flavor of the pepper is well retained. However, the salt content in the pepper is too high, and long-term consumption of the pepper may cause damage to human body.

Therefore, it is of great significance for the fermentation process of pickles to seek a starter culture for fermentation that has high acid production and high tolerance, and can reduce the nitrite content.

SUMMARY OF THE INVENTION

The present invention provides a *Lactobacillus plantarum*, which has high acid production and high tolerance, and can effectively reduce the nitrite content during the production of pickles.

Technical solutions of the present invention:

A *Lactobacillus plantarum* tlj-2014 is provided, which is deposited on Jul. 2, 2014 in China General Microbiological Culture Collection Center (CGMCC) (Institute of Microbiology, Chinese Academy of Sciences, No. 1 West Beichen Road, Chaoyang District, Beijing, China, 100101) under CGMCC Accession No. 9405. The strain was deposited at CGMCC under the Budapest Treaty and will be made available to the public upon issuance of a patent.

The *Lactobacillus plantarum* tlj-2014 is bred by the following process:

original starting strain→in vitro activation→diethyl sulfate (DES) mutagenesis→nitrosoguanidine (NTG) mutagenesis→plasma mutagenesis primary screening by plate culture→secondary screening by shake flask culture→passage stability test The *Lactobacillus plantarum* tlj-2014 is characterized in that (1) with the strain, the lactic acid production rate can be up to 35 g/L/d, and the concentration of lactic acid after 71 hrs of fermentation is up to 95 g/L;

(2) the strain is acid tolerant, and survives well at pH 1.80; and (3) the strain can degrade the nitrite quickly with a decomposition capability of up to 9.8 mg/h/kg (the accumulation rate of the nitrite in the spontaneous fermentation process is about 1.1 mg/h/kg), and is tolerant to 1% bile salt.

Beneficial Effects

It is found through tests that the *Lactobacillus plantarum* tlj-2014 provided in the present invention is strongly genetically stable, since it can be continuously slant-subcultured for 10 generations without obvious change in traits and with various performance criteria kept normal. With the strain, the lactic acid production rate can be up to 35 g/L/d, and the concentration of lactic acid after 71 hrs of fermentation is up to 95 g/L. The *Lactobacillus plantarum* tlj-2014 which can survive at pH 1.80, is tolerant to 1% bile salt, and can degrade the nitrite quickly with a decomposition capability of up to 9.8 mg/h/kg. When the strain is used in production of pickles, the nitrite concentration is lower than 5 mg/kg throughout the entire fermentation process, which is far below the content (20 mg/kg) specified in the national standard GB2714-2003.

DETAILED DESCRIPTION OF THE INVENTION

Example 1

Characteristics of the Strain

The *Lactobacillus plantarum* tlj-2014 is deposited on Jul. 2, 2014 in China General Microbiological Culture Collection Center (CGMCC) (Institute of Microbiology, Chinese Academy of Sciences, Building 3, No. 1 West Beichen Road, Chaoyang District, Beijing, China, 100101) under CGMCC Accession No. 9405.

The strain has the following features. When observed under a microscope, the strain is short rod-like and gram positive, has no flagellum, and is asporulate. When cultured on a solid medium, the *Lactobacillus plantarum* tlj-2014 forms a white colony, which has a smooth surface, and is dense and in a circular morphology with a regular edge.

The physiochemical properties include hydrogen peroxidase (−), gelatine liquefication (−), indole test (+), mobility (−), gas from fermentation (−), nitrite reduction (−), gas from fermentation (−), hydrogen sulfide production (−), and growth in MRS medium pH 4.0 (+).

Example 2—Screening of the Strain

The *Lactobacillus plantarum* tlj-2014 according to the present invention was screened from the original starting strain *Lactobacillus plantarum* L after mutagenesis, and the original starting strain *Lactobacillus plantarum* L was collected by Li Zheng from the ensilage in a sheep breezing farm in Yanchi, Ningxia on Sep. 15, 2013.

When grown in a MRS medium with glucose, the starting strain had a lactic acid production rate of 1.5 g/L/d, almost stopped growing when the culture medium reached pH 3.5, and had a decomposition rate for sodium nitrite of 0.34 mg/h/kg of Chinese cabbage.

In order to improve the lactic acid production rate, the acid tolerance, and the nitrite decomposition rate, the strain was subjected to DES and NTG mutagenesis sequentially. After mutagenesis, the strains were primarily screened in a plate containing MRS supplemented with calcium carbonate, and then the high production strains were secondarily screened by fermentation in a 500 mL shake flask using a biosensor analyzer, to breed a good *Lactobacillus plantarum* strain. Subsequently, passage test was carried out to evaluate the genetic stability. The specific operations were as follows.

1. Breeding by DES Mutagenesis (1) The *Lactobacillus plantarum* L was picked up by using an inoculating loop from the test-tube slant on a super clean bench, inoculated in a 250 mL conical flask containing 50 mL MRS medium (agar free, and containing 20 g/L of glucose), and incubated at 200 rpm and 37° C. for about 12 hrs, such that the bacteria were in an earlier exponential growth phase.

(2) 5 mL of the culture was centrifuged at 5000 rpm for 10 min, to collect a bacterial pellet, which was then washed 2 times with saline.

(3) The bacteria pellet was diluted with a phosphate buffer (pH 7.0) to a density of $10^7$ cells/mL of the bacterial suspension.

(4) 32 mL of a potassium phosphate buffer (pH 7.0), 8 mL of the bacterial suspension, and 0.4 mL DES were fully mixed in a 150 mL conical flask in which a rotor was placed in advance, such that the final concentration of DES was 1% (v/v).

(5) The reaction was continued for 30 min at 37° C. in a shaker at 150 rpm, and 1 mL of the mixture was removed, to which 0.5 mL of a 25% $Na_2S_2O_3$ solution was added to quench the reaction.

(6) The bacteria were appropriately diluted, and then 0.2 mL of the finally diluted bacterial suspension was removed and transferred to a flat plate containing a screening medium containing calcium carbonate (MRS medium supplemented with calcium carbonate and containing 100 g/L of glucose). After incubation at 37° C. for 2-3 days, the strain in the screening plate was transferred by replica plating to an LPHMRS medium (a low pH modified MRS medium) having a pH value of 1.5, 1.8, and 2.0 and a screening medium containing sodium nitrite (modified MRS screening medium with 2 g/L of sodium nitrite as a nitrogen source alone).

(7) After incubation at 37° C. for 2-3 days, the strain that had a large colony, and could grow respectively in the LPHMRS medium and the screening medium containing sodium nitrite was selected. The colony picked up after primary screening in a screening medium containing calcium carbonate was designated as *Lactobacillus plantarum* L1.

2. Nitrosoguanidine (NTG) Mutagenesis (1) The *Lactobacillus plantarum* L1 was picked up by using an inoculating loop from the test-tube slant on a super clean bench, inoculated in a 250 mL conical flask containing 50 mL MRS medium (agar free, and containing 60 g/L of glucose), and incubated at 200 rpm and 37° C. for about 12 hrs, such that the bacteria were in an earlier exponential growth phase.

(2) 5 mL of the culture was centrifuged at 5000 rpm for 10 min, to collect a bacterial pellet, which was then washed 2 times with saline.

(3) The bacteria pellet was diluted with a phosphate buffer (pH 6.0) to a density of $10^7$ cells/mL of the bacterial suspension.

(4) 10 mL of the bacterial suspension was transferred to a 100 mL conical flask, to which 10 mg NTG was added to formulate an NTG solution at a final concentration of 10 mg/mL, and 4-5 drops of acetone was also added to facilitate the dissolution of NTG.

(5) The reaction was shaken for 30 min at 37° C. at 200 rpm, and then centrifuged at 5000 rpm for 10 min, to collect a bacterial pellet, which was then washed several times with sterile saline to quench the reaction.

(6) The bacterial pellet was appropriately diluted, and then 0.2 mL of the finally diluted bacterial suspension was removed and transferred to a flat plate containing a screening medium containing calcium carbonate (MRS medium supplemented with calcium carbonate and containing 100 g/L of glucose). After incubation at 37° C. for 2-3 days, the strain in the screening plate was transferred by replica plating to an LPHMRS medium (a low pH modified MRS medium) having a pH value of 1.5, 1.8, and 2.0 and a screening medium containing sodium nitrite (modified MRS screening medium with 2 g/L of sodium nitrite as a nitrogen source alone).

(7) The strain that had a large colony, and could grow respectively in the LPHMRS medium and the screening medium containing sodium nitrite was selected. 100 colonies meeting the above criteria were picked up after primary screening in a screening medium containing calcium carbonate.

3. Secondary Screening by Shake Flask Culture (1) The *Lactobacillus plantarum* was picked up by using an inoculating loop respectively from each of the test-tube slants on a super clean bench, inoculated in a 250 mL conical flask containing 50 mL MRS medium (agar free, and containing 100 g/L of glucose), and incubated at 200 rpm and 37° C. for about 15 hrs, such that the bacteria were in a middle exponential growth phase.

(2) 5 mL of the culture was inoculated respectively into a flat plate containing 50 mL of a liquid screening medium containing calcium carbonate (MRS medium supplemented with calcium carbonate and containing 250 g/L of glucose), and in an liquid LPHMRS medium (a low pH modified MRS medium) having a pH value of 1.5, 1.8, and 2.0 and a liquid screening medium containing sodium nitrite (modified MRS screening medium with 2 g/L of sodium nitrite as a nitrogen source alone) (note: in a 250 mL conical flask). The incubation was continued at 200 rpm and 37° C. for 3-4 days. The production rate of L-lactic acid in the liquid screening medium containing calcium carbonate, the bio-mass in the liquid LPHMRS medium, and the consumption rate of the nitrite in the liquid screening medium containing sodium nitrite were respectively detected daily. After completion of the fermentation, the production rate of L-lactic acid in the liquid screening medium containing calcium carbonate, the bio-mass in the liquid LPHMRS medium, and the consumption rate of the nitrite in the liquid screening medium containing sodium nitrite were compared for the 100 strains.

(3) The strain having high L-lactic acid production rate, low pH tolerance (the strain could merely grow in a culture medium having a pH not lower than 1.8), and high nitrite consumption rate was selected, and designated as *Lactobacillus plantarum* L2.

4. Genetic Stability Test

The *Lactobacillus plantarum* L2 was continuously slant-subcultured for 10 generations, and the fermentations with each subculture were detected by secondary screening by shake flask culture. It was found through tests that the strain can be continuously slant-subcultured for 10 generations without obvious change in traits and with various performance criteria kept normal, suggesting that the strain is strongly genetically stable. The strain was designated as *Lactobacillus plantarum* tlj-2014.

Example 3 Tests in 5 L Fermentor (1) The *Lactobacillus plantarum* L2 was picked up by using an inoculating loop from the test-tube slant, inoculated in a 250 mL conical flask containing 50 mL MRS medium (agar free, and containing 150 g/L of glucose), and incubated at 200 rpm and 37° C. for about 12 hrs, such that the bacteria were in a middle exponential growth phase.

(2) The strain in the exponential phase was inoculated in a 5 L fermentor containing 3 L of a liquid MRS medium (with glucose in an initial concentration of 150 g/L) in an amount of 10%, and incubated at 37° C. and 100 rpm for 8 hrs. The dissolved oxygen was controlled to be 10% (through aeration at a rate of 0.5 L/min) in the earlier exponential phase, and then anaerobic incubation was continued for 63 hrs in the later phase. After fermentation, the *Lactobacillus plantarum* L2 was shown to have a lactic acid production of 95 g/L. Such a lactic acid production rate can promote the rapid fermentation of pickles.

(3) The strain in the exponential phase was inoculated in a 5 L fermentor containing 3-L of a liquid LPHMRS medium (pH 1.8, with glucose in an initial concentration of 50 g/L) in an amount of 10%, and incubated at 37° C. and 100 rpm for 8 hrs. The dissolved oxygen was controlled to be 10% (through aeration at a rate of 0.5 L/min) in the earlier exponential phase, and then anaerobic condition was maintained in the later phase. The fermentation liquor was controlled to be pH 1.8 with 0.5 mol/L sodium hydroxide throughout the entire process, and the incubation time was 48 hrs in total. After fermentation, the biomass of *Lactobacillus plantarum* L2 was detected to be 2.5 g/L, indicating that the *Lactobacillus* plantar=L2 could survive in an environment at pH 1.8.

(4) The strain in the exponential phase was inoculated in a 5 L fermentor containing 3 L of a liquid screening medium containing sodium nitrite (modified MRS screening medium with 2 g/L of sodium nitrite as a nitrogen source alone) in an amount of 10%, and incubated at 37° C. and 100 rpm for 8 hrs. The dissolved oxygen was controlled to be 10% (through aeration at a rate of 0.5 L/min) in the earlier exponential phase, and then anaerobic condition was maintained in the later phase. During the fermentation, 20 g/L of a sodium nitrite solution was fluidically added, depending on the consumption rate of the nitrite. The incubation was continued for 2-3 days. After fermentation, the degradation rate of sodium nitrite by *Lactobacillus Plantarum* L2 during fermentation was calculated. The results showed that the degradation rate of sodium nitrite by *Lactobacillus Plantarum* L2 under these conditions can be up to 563 mg/h/L.

(5) 10 mL of the strain in the exponential phase was inoculated to 2 kg of pretreated Chinese cabbage, to produce a pickle following the conventional process. The nitrite content in the pickle was determined every 12 hrs. The results showed that throughout the entire fermentation process, the decomposition rate of sodium nitrite by *Lactobacillus Plantarum* L2 is 9.8 mg/h/kg of Chinese cabbage. The nitrite content in the pickle is consistently lower than 5 mg/kg, which is far below the content (20 mg/kg) specified in the national standard GB2714-2003.

The invention claimed is:

1. An isolated biologically pure culture of strain *Lactobacillus plantarum* tlj-2014 (CGMCC 9405) obtained by a selective mutation breeding.

2. The *Lactobacillus plantarum* tlj-2014 according to claim 1, characterized in that with the *Lactobacillus plantarum*, the lactic acid production rate can be up to 35 g/L/d, and the concentration of lactic acid after 71 hrs of fermentation is up to 95 g/L.

3. The *Lactobacillus plantarum* tlj-2014 according to claim 1, characterized in that the *Lactobacillus plantarum* is acid tolerant, and survives well at pH 1.80.

* * * * *